(12) United States Patent
Goddard et al.

(10) Patent No.: US 9,316,579 B2
(45) Date of Patent: Apr. 19, 2016

(54) METHOD AND APPARATUS FOR OPTICAL SENSING USING AN OPTICAL SENSOR INCLUDING A LEAKY MODE WAVEGUIDE

(75) Inventors: Nicholas John Goddard, Manchester (GB); Paul Taylor, Manchester (GB)

(73) Assignee: EMD MILLIPORE CORPORATION, Billerica, MA (US)

( * ) Notice: Subject to any disclaimer, the term of this patent is extended or adjusted under 35 U.S.C. 154(b) by 695 days.

(21) Appl. No.: 13/509,502

(22) PCT Filed: Nov. 10, 2010

(86) PCT No.: PCT/GB2010/002067
§ 371 (c)(1),
(2), (4) Date: Oct. 3, 2012

(87) PCT Pub. No.: WO2011/058308
PCT Pub. Date: May 19, 2011

(65) Prior Publication Data
US 2013/0119242 A1 May 16, 2013

(30) Foreign Application Priority Data

Nov. 11, 2009 (GB) .................................. 0919742.7

(51) Int. Cl.
*G01D 5/353* (2006.01)
*G02B 6/43* (2006.01)
(Continued)

(52) U.S. Cl.
CPC .............. *G01N 21/17* (2013.01); *G01N 21/553* (2013.01); *G01N 21/7703* (2013.01); *G01N 33/54373* (2013.01); *G01N 2021/7776* (2013.01); *G01N 2333/922* (2013.01); *G01N 2600/00* (2013.01)

(58) Field of Classification Search
CPC ............ G01N 21/533; G01N 21/7703; G01N 33/54373; G01N 21/17; G01N 2333/922; G01N 2600/00; G01N 2021/7776
USPC ............ 385/12, 14, 15, 16, 33, 129; 356/244, 356/445, 351; 372/64; 438/765, 780, 795; 427/100, 255.18
See application file for complete search history.

(56) References Cited

U.S. PATENT DOCUMENTS 5,567,794 A * 10/1996 Barraud et al. .................. 528/70
6,483,959 B1 * 11/2002 Singh et al. ..................... 385/12
(Continued)

FOREIGN PATENT DOCUMENTS

WO     9944042     9/1999
WO     WO0046589 A1    8/2000
(Continued)

OTHER PUBLICATIONS

Multiple surface plasmon resonance quantification of dextromethorphan using a molecularly imprinted beta-cyclodextrin polymer. A potential probe for drug-drug interaction.
(Continued)

*Primary Examiner* — Akm Enayet Ullah
(74) *Attorney, Agent, or Firm* — Brian W. Chellgren; John V. Daniluck; Bingham Greenebaum Doll LLP

(57) ABSTRACT

An optical sensor comprising a waveguide having a sensing layer which is molecularly imprinted such that it will receive and retain target entities to be sensed, the optical sensor further comprising a detection apparatus arranged to detect a change of an optical property of the waveguide which occurs when the target entities are received and retained in the sensing layer.

9 Claims, 8 Drawing Sheets

(51) Int. Cl.
*G01N 21/17* (2006.01)
*G01N 21/552* (2014.01)
*G01N 21/77* (2006.01)
*G01N 33/543* (2006.01)

(56) References Cited

U.S. PATENT DOCUMENTS

| | | | |
|---|---|---|---|
| 6,527,961 B1 * | 3/2003 | Vigna et al. | 216/2 |
| 6,670,286 B1 | 12/2003 | Yang et al. | |
| 7,190,851 B2 * | 3/2007 | Grace et al. | 385/12 |
| 8,629,981 B2 * | 1/2014 | Martini et al. | 356/417 |
| 2004/0058380 A1 | 3/2004 | Levon et al. | |
| 2006/0147147 A1 * | 7/2006 | Zourob et al. | 385/12 |
| 2007/0059211 A1 * | 3/2007 | Edmiston | 422/82.11 |
| 2009/0281272 A1 | 11/2009 | Yilmaz et al. | |
| 2010/0098592 A1 * | 4/2010 | Rong et al. | 422/82.11 |

FOREIGN PATENT DOCUMENTS

| WO | WO2004031743 A1 | 4/2004 |
|---|---|---|
| WO | WO2004081572 A1 | 9/2004 |
| WO | WO2007109096 A2 | 9/2007 |

OTHER PUBLICATIONS

Roche, P., et al., Sensors and Actuators B, May 20, 2009, vol. 139, No. 1, pp. 22-29.

Synthetic receptors as sensor coatings for molecules and living cells. Dickert F et al., Analyst; Jun. 1, 2001, vol. 126, No. 6, pp. 766-771.

Qi, Zhi-Mei, et al., Nanoporous leaky waveguide based chemical and biological sensors with broadband spectroscopy, Applied Physics Letters, vol. 90, 011102 Jan. 2, 2007.

\* cited by examiner

METHOD AND APPARATUS FOR OPTICAL SENSING USING AN OPTICAL SENSOR INCLUDING A LEAKY MODE WAVEGUIDE

CROSS REFERENCE TO RELATED APPLICATIONS

This application is a U.S. National Stage application of International Patent Application No. PCT/GB2010/002067, filed Nov. 10, 2010, which claims priority to GB Patent Application Ser. No. 0919742.7, filed Nov. 11, 2009, both of which are incorporated herein by reference.

The present invention relates to an optical sensor and to a method of optical sensing.

Sensors which are capable of monitoring biological interactions with high sensitivity and in real-time are of considerable importance within both life science research and industry. Several sensors exist which monitor changes in refractive index (or other optical properties) of a biological sample as a result of molecular interactions. Such changes in the optical properties of the sample may be measured as a change in a property of the light passing through the sample, such as the intensity.

In a typical sensor, light is coupled into a guided mode of an optical waveguide. An evanescent wave associated with the guided mode extends into a biological sample, which may for example be held in a gel or be in liquid form. In some sensors it is possible to tune the depth to which the evanescent wave extends into the biological sample by altering the incident angle at which the light is coupled into the waveguide. If a change occurs in the biological sample then the refractive index of the biological sample will change. This change of the refractive index is experienced by the evanescent wave associated with the guided mode. Changes occurring in the biological sample may therefore be observed by monitoring light output from the guided mode of the optical waveguide.

It is desirable to detect contaminants within water. This is particularly the case for ultra-pure water, which may for example be used for chemical assays or intravenous injections. In this case, not only should the water be free from biological agents such as bacteria, but it should also be free of the endo-toxins which they produce.

Some methods of detecting bacteria in water detect the action of live bacteria and hence are insensitive to endo-toxins. They are also insensitive to dead bacteria or broken-down bacteria. Other methods detect the action of enzymes which indicate the recent presence of bacteria. However, in order for this to work the enzymes must not have been denatured. That is, they must still function in order that their action can be detected. Both of the above methods typically require the use of additional reagents.

It is possible to detect endo-toxins using prior art methods. However, the methods used to detect endo-toxins typically require controlled conditions and the use of additional reagents. One such method involves the use of amoebocyte blood cells of a horseshoe crab (*Limulus polyphemus*). The blood cells form clots when placed in contact with a bacterial endo-toxin, even in very low endo-toxin concentrations.

The above methods of detecting bacteria and endo-toxins are inefficient and may be ineffective in some circumstances. Furthermore, they do not lend themselves to continuous monitoring of water for contaminants.

It is desirable to overcome or mitigate at least one of the above disadvantages.

According to a first aspect of the present invention there is provided an optical sensor comprising a waveguide having a sensing layer which is molecularly imprinted such that it will receive and retain target entities to be sensed, the optical sensor further comprising a detection apparatus arranged to detect a change of an optical property of the waveguide which occurs when the target entities are received and retained in the sensing layer.

The sensing layer may comprise reception sites having shapes which are suitable for receiving the target entities.

The sensing layer may comprise reception sites having functional groups which are complementary to functional groups of the target entities.

The sensing layer may be porous.

The optical property in which a change is detected may be the refractive index.

The target entities may be an organophosphate compound or bio-molecule, such as ribonuclease, which may be inactive.

The waveguide may be a leaky mode waveguide.

The waveguide may include a layer of material having a refractive index which is higher than the refractive index of the sensing layer. The layer of material may be a metal layer.

The sensing layer may be a polymer layer The polymer may be a carbon or silicon based polymer.

The sensor may form part of a contamination detector which is part of a water purification system.

According to a second aspect of the invention there is provided a method of optical sensing using an optical sensor comprising a waveguide having a sensing layer which is molecularly imprinted such that it will receive and retain target entities, the method comprising locating a portion of the sensor in a fluid flow path, the fluid flowing so as to contact at least a surface of the sensing layer, coupling light into a guided mode of the waveguide such that the sensing layer receives at least some of the light, and monitoring a property of light output from the waveguide, the property changing in the event that target entities are received and retained in the molecularly imprinted layer.

The sensing layer may be porous with respect to the flowing fluid, thereby allowing the fluid to flow into the sensing layer.

The sensing layer may comprise reception sites having shapes which are suitable for receiving the target entities.

The sensing layer may comprise reception sites having functional groups which are complementary to functional groups of the target entities.

The property of output light which is monitored may be the intensity of light and/or the angle at which light is output from the waveguide.

The entities to be sensed may be ribonuclease, which may be inactive.

The fluid may be water.

The entities to be sensed may be a contaminant or a product of a contaminant.

Other preferred and advantageous features of the various aspects of the present invention will be apparent from the following description.

Specific embodiments of the present invention will now be described, by way of example only, with reference to the accompany drawings, in which.

Figure 2:
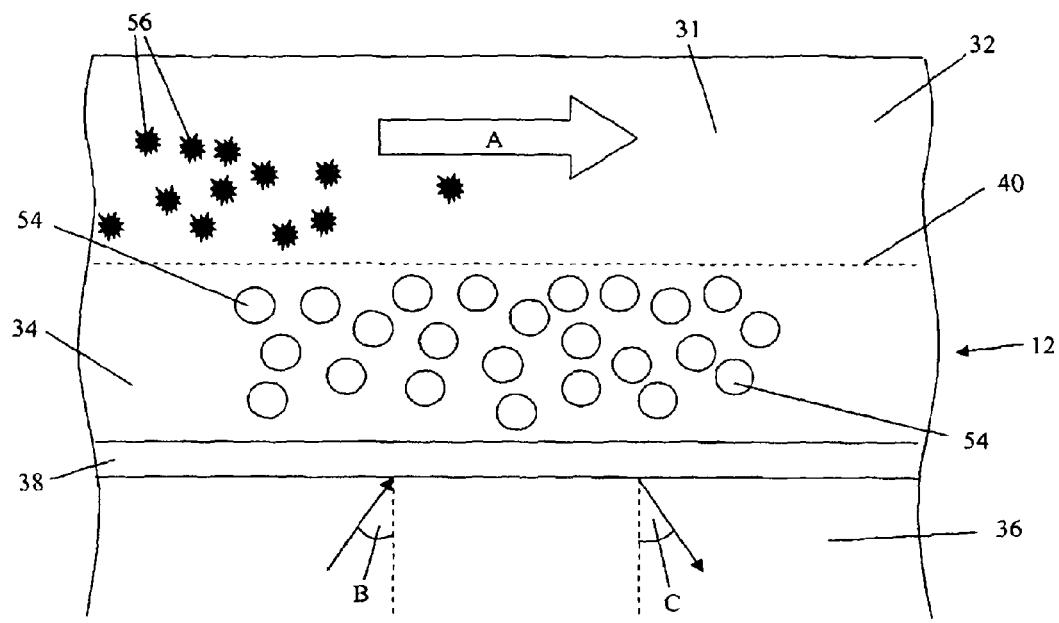
FIGS. 2 and 3 are schematic cross-sectional views of a waveguide of the optical sensor shown in FIG. 1.
Figure 3:
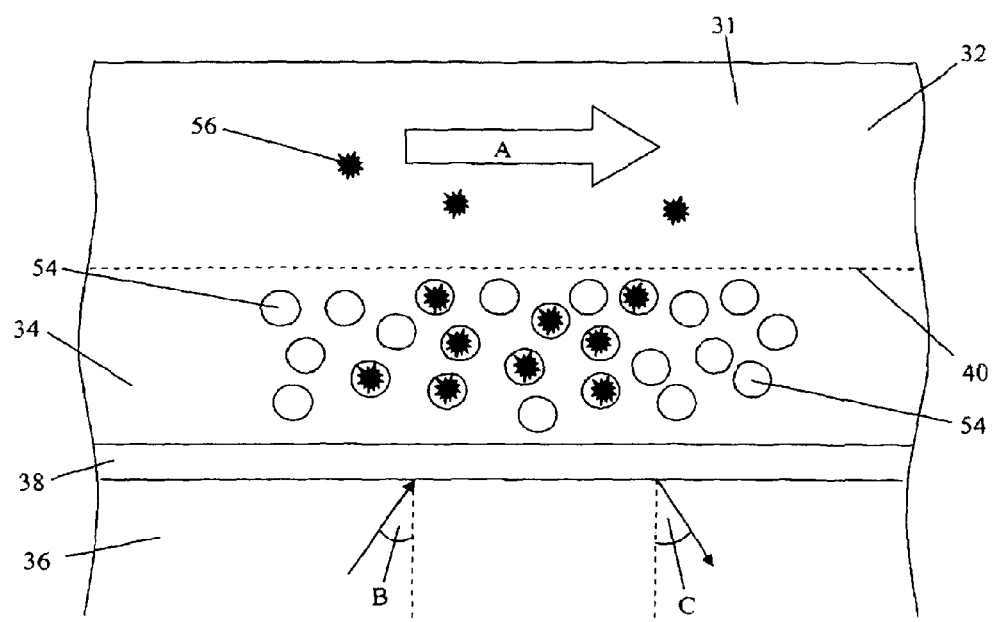
Figures 4A, 4B, 4C:
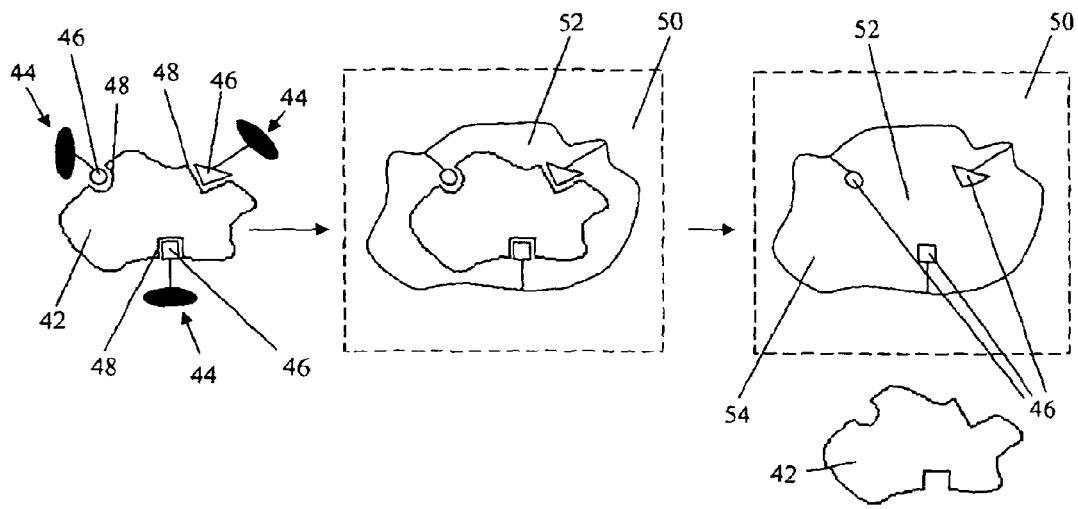
Figure 5:
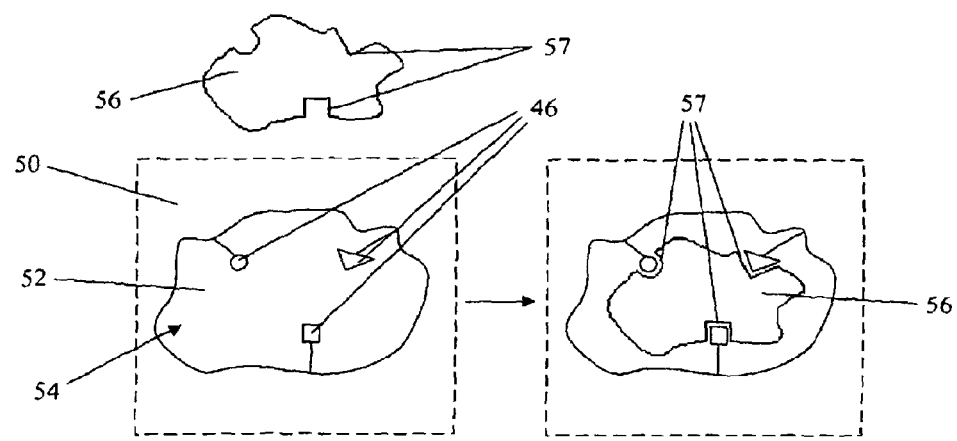
Figure 6:
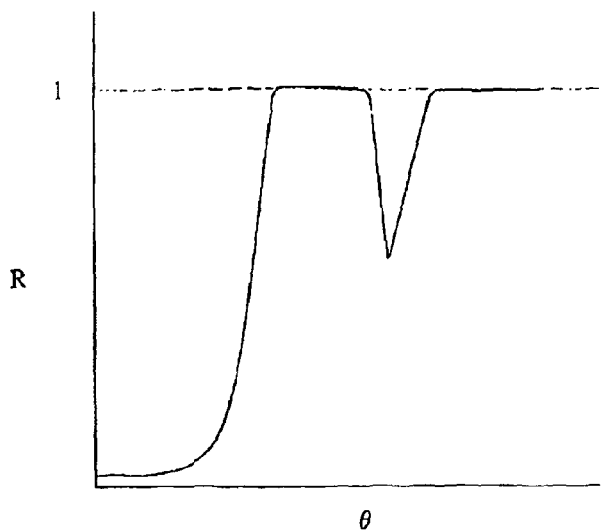
Figure 7:
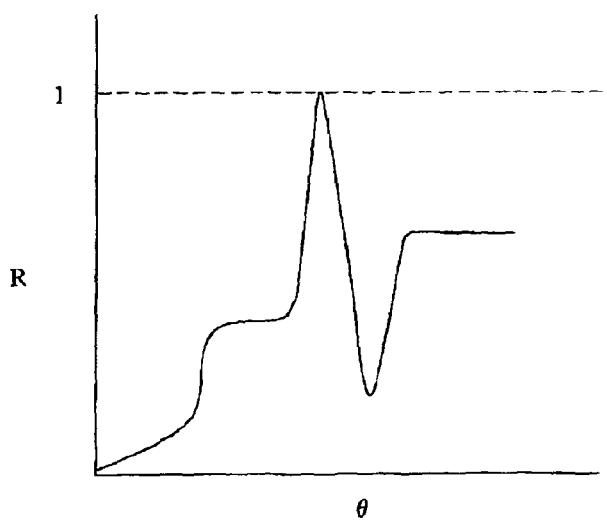
Figure 8:
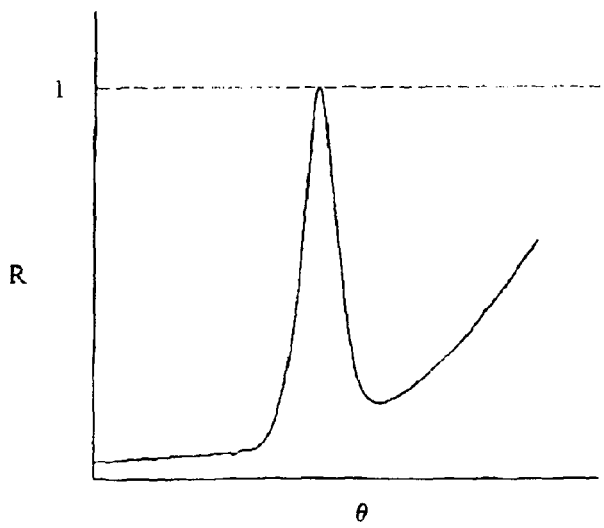
Figure 9:
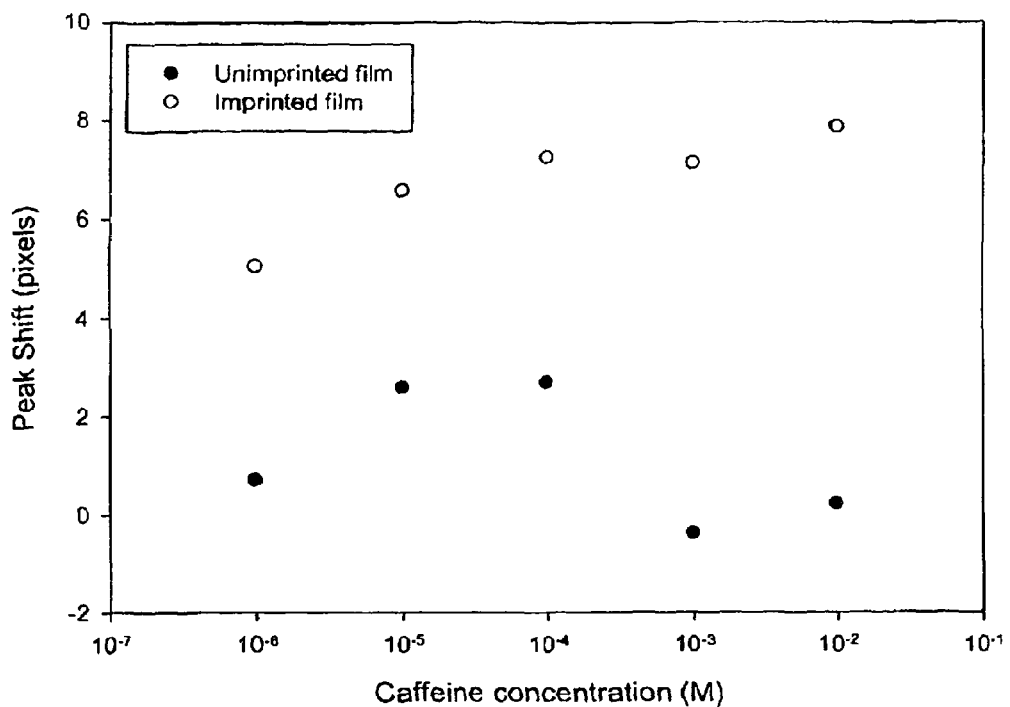
Figure 10:
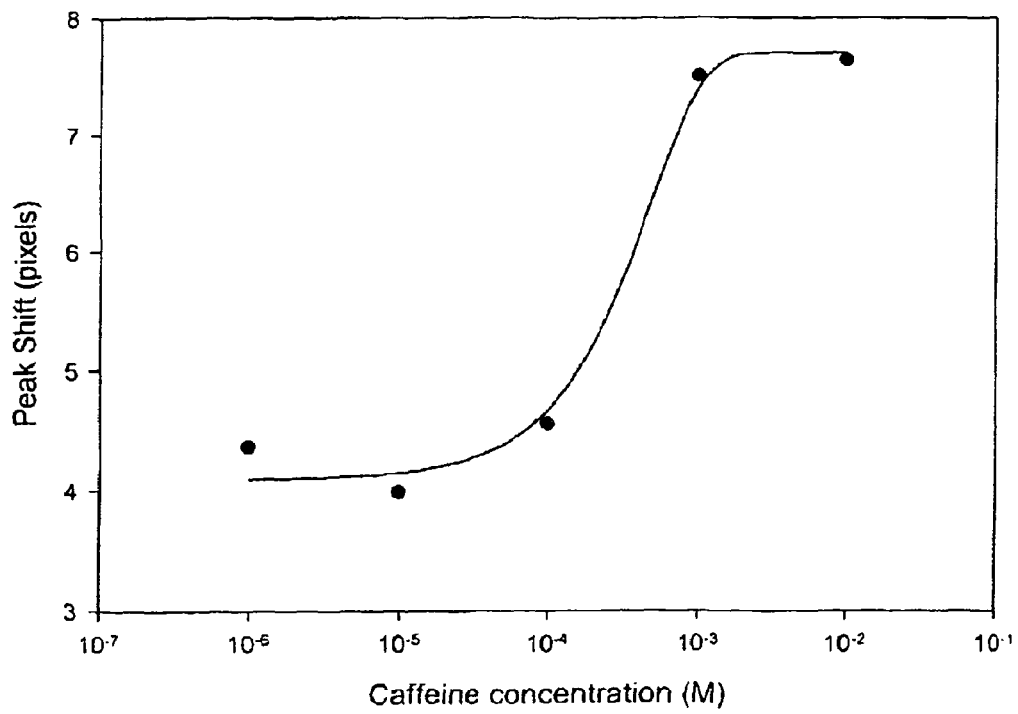
Figure 11:
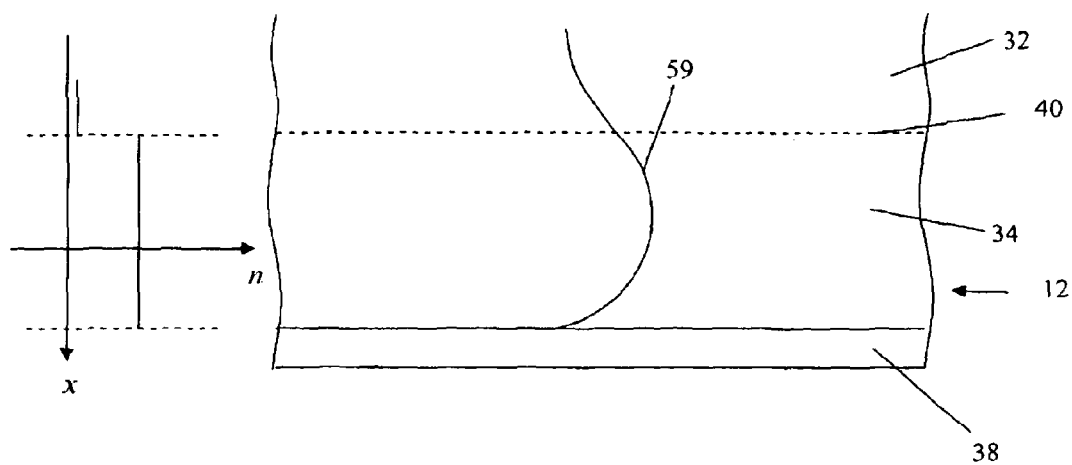
Figure 12:
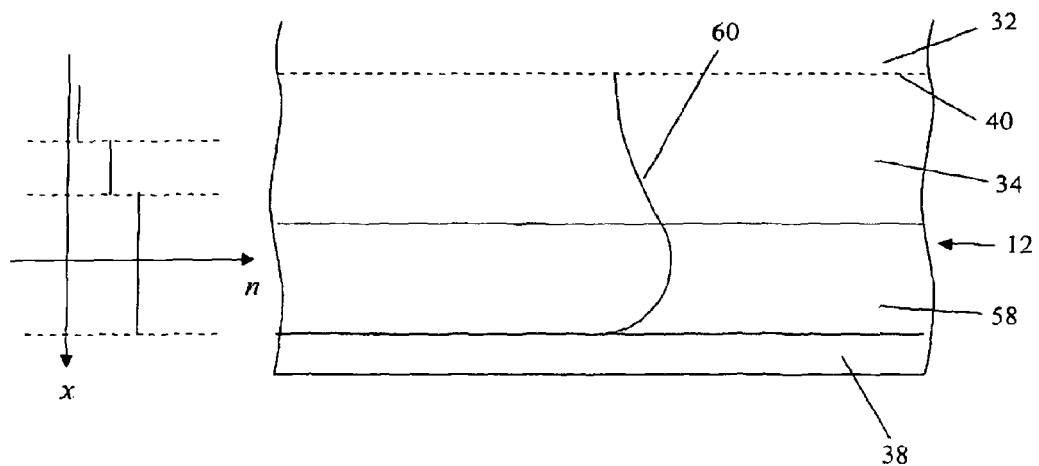
Figure 13:
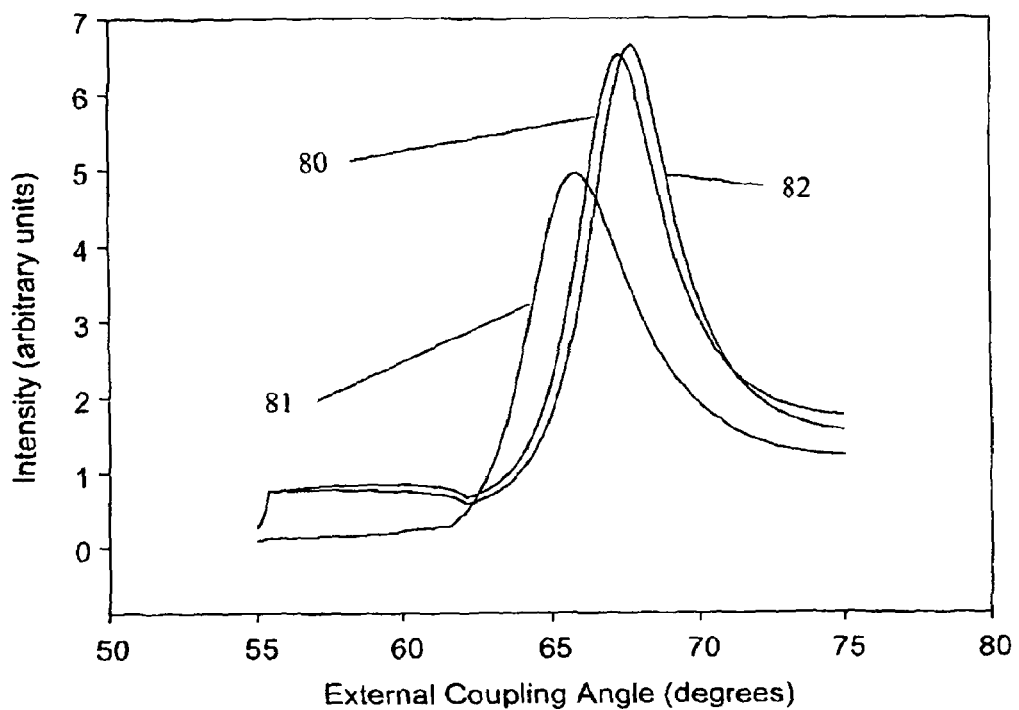
Figure 14:
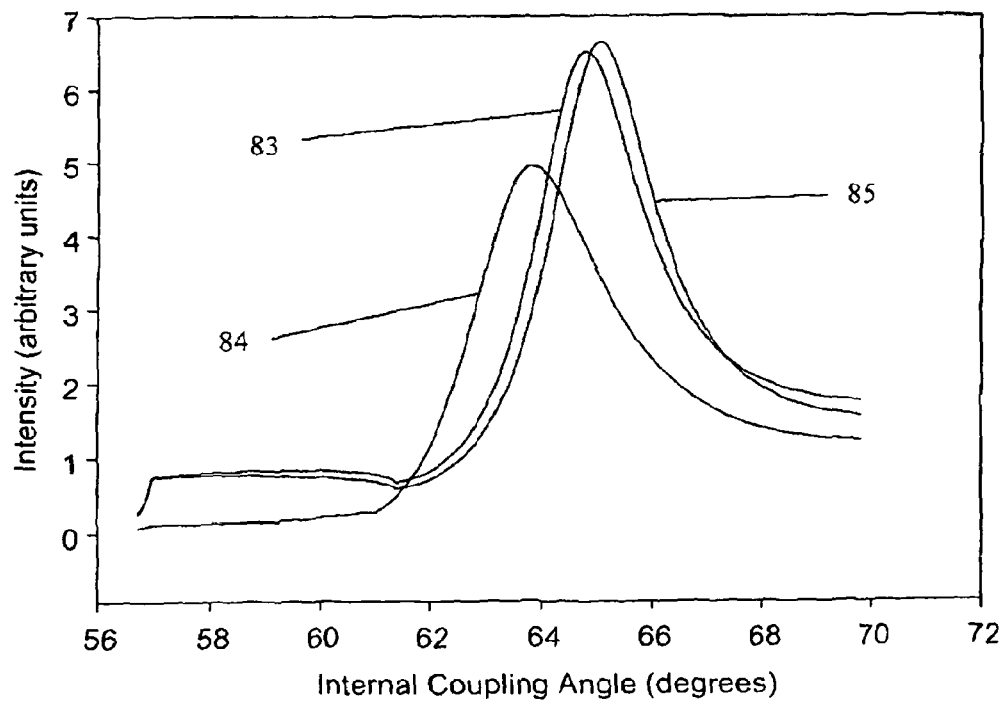
Figure 15:
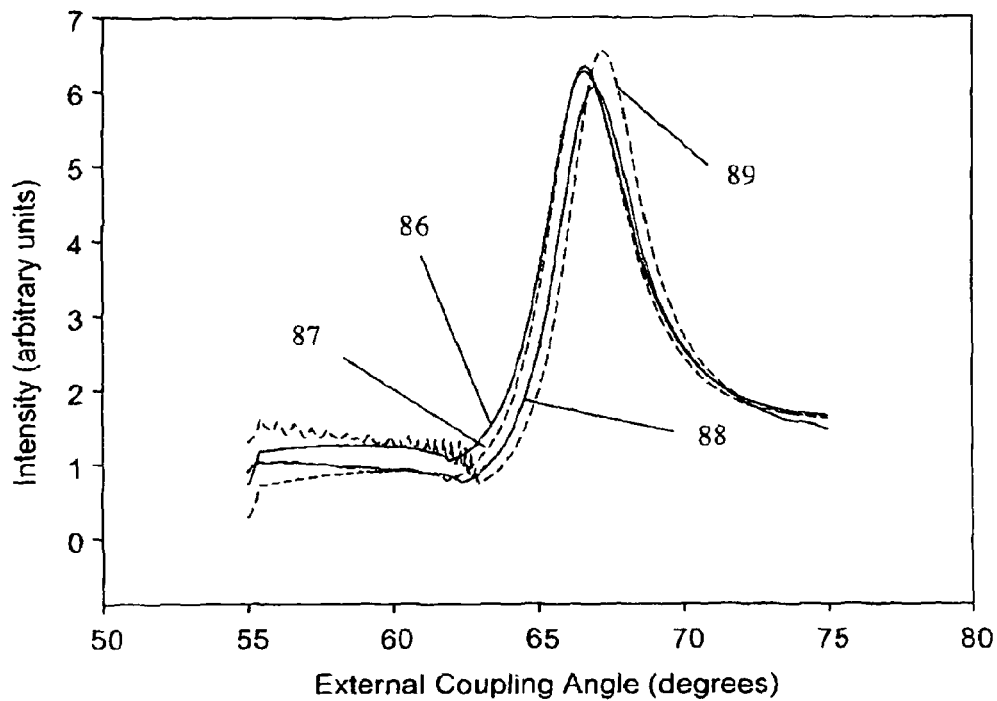
Figure 16:
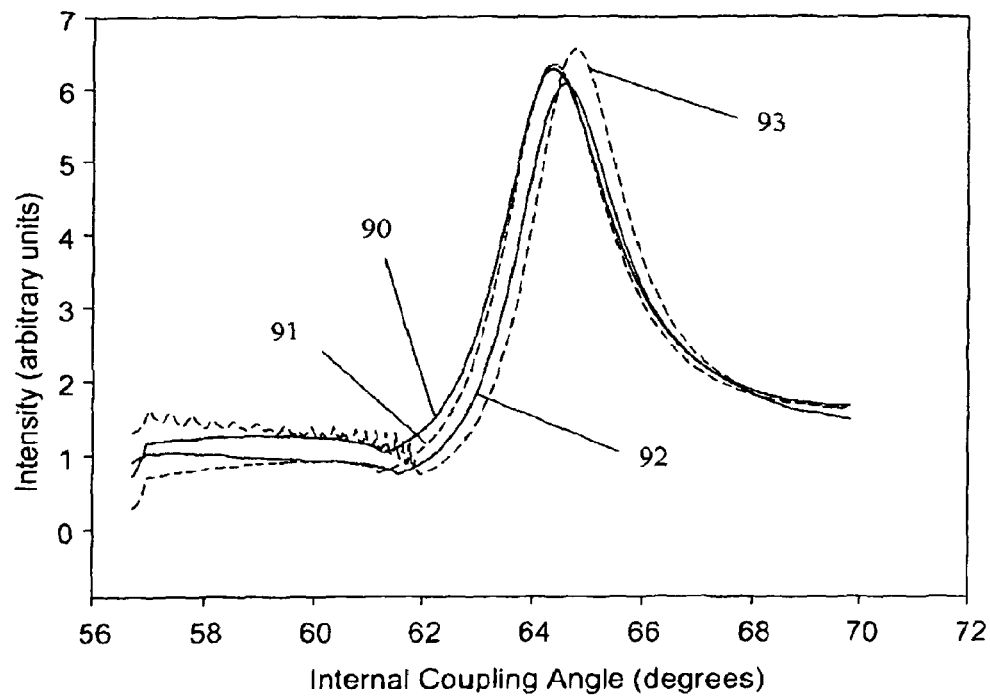

FIGS. 4*a*, 4*b* and 4*c* are diagrams of a process used to create a molecularly imprinted polymer in accordance with the present invention;

FIG. 5 is a diagram of a process by which a target entity is received by a molecular polymer cavity created by the process shown in FIGS. 4*a* to 4*c*;

FIG. 6 is a graph showing a first general scheme of the relationship between the reflectivity of a waveguide and the angle at which light is incident on the waveguide;

FIG. 7 is a graph showing a second general scheme of the relationship between the reflectivity of a waveguide and the angle at which light is incident on the waveguide;

FIG. 8 is a graph showing a third general scheme of the relationship between the reflectivity of a waveguide and the angle at which light is incident on the waveguide;

FIG. 9 is a graph showing the difference between the position of a peak pixel and a baseline pixel as a function of concentration of a target entity to which a waveguide is exposed to for two separate waveguides, one of which comprises a molecularly imprinted polymer sensing layer in accordance with an embodiment of the invention and the other of which comprises a non molecularly imprinted polymer sensing layer;

FIG. 10 is a graph showing, as a function of concentration of a target entity exposure, the difference between the position of the peak pixel using a waveguide which comprises a molecularly imprinted polymer sensing layer according to the present invention and using a waveguide which has a non molecularly imprinted polymer sensing layer;

FIG. 11 is a schematic cross-sectional view of the waveguide of the optical sensor shown in FIGS. 2 and 3 and a corresponding graph of refractive index;

FIG. 12 is a schematic cross-sectional view of an alternative waveguide of the optical sensor and a corresponding graph of refractive index;

FIG. 13 is a graph showing a first response of several waveguides which may form part of an optical sensor according to the invention, each of the waveguides having a molecularly imprinted polymer layer which has been spin coated using different parameters;

FIG. 14 is a graph showing a second response of the waveguides of FIG. 13;

FIG. 15 is a graph showing a first response of a waveguide, which may form part of an optical sensor according to the invention, in several conditions; and FIG. 16 is a graph showing a second response of the waveguide of FIG. 15 in said several conditions.

Figure 1:
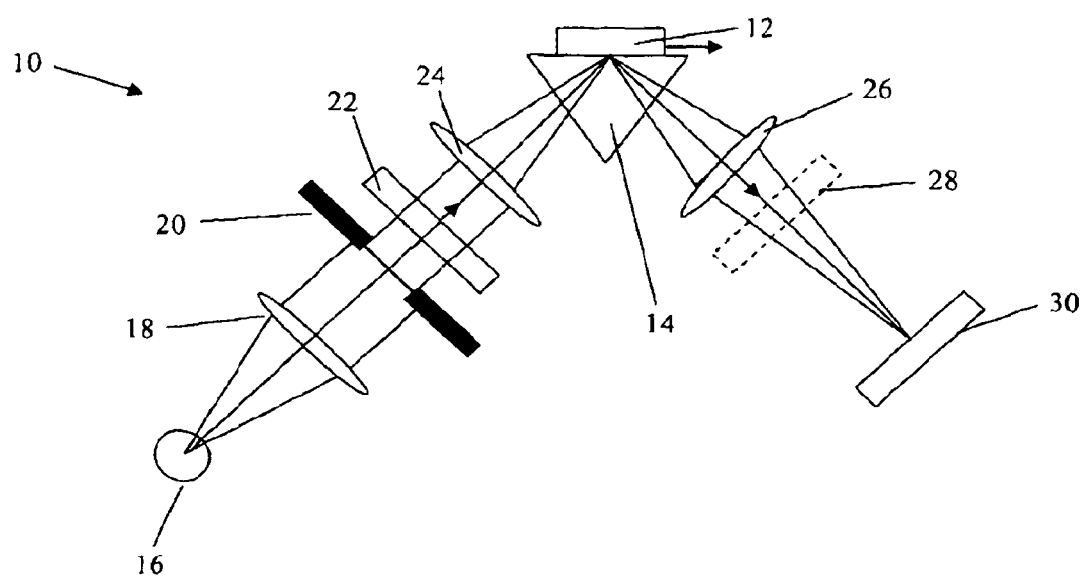
FIG. 1 is a schematic cross-sectional view of an optical sensor in accordance with an embodiment of the present invention.

Referring to FIG. 1, an optical sensor 10 comprises a waveguide 12 located on a prism 14. Light from a light source 16 is directed towards the waveguide 12 via a collimating lens 18, an aperture stop 20, a first polariser 22, a first converging lens 24 and the prism 14. The polariser 22 is used to select an appropriate polarisation of light. The light enters the waveguide via the prism, which couples light into the waveguide. Some of the light subsequently leaks out of the waveguide 12 and passes though the prism 14. The light travels from the prism 14 via a second converging lens 26, a second polariser 28 which is crossed relative to the first polariser 22, and into a detector 30. The detector 30 is a light intensity detector such as a photodiode or CCD array. Any suitable radiation detector may be used. In some embodiments the second polariser 28 may be omitted.

FIG. 2 shows part of the waveguide 12 in more detail. The waveguide 12 comprises a sensing layer 34 provided on a metal layer 38. The waveguide 12 is situated in flow communication with a conduit 32 through which a fluid 31 flows (flow denoted by arrow A). The metal layer 38 is provided on a substrate 36. The substrate, which may for example be formed from quartz, may be bonded to the prism 14 (see FIG. 1). The prism 14 may be used to couple light into and out of the waveguide 12. In some embodiments the metal layer 38 has a thickness of 20 nm. However, any appropriate thickness of metal layer 38 may be used. The thickness of the metal layer 38 may be for example between 0.5 nm and 200 nm.

The sensing layer 34 is a polymer layer, which may for example be carbon or silicon based. An advantage of silicon-based polymers, compared to similar carbon based ones, is that they can be produced in the presence of air. This is not possible using carbon based polymers because they react with oxygen in the air. In particular, if the carbon based polymer is formed by a free radical polymerisation process, then the oxygen will react with the free radicals. Silicon-based polymers may comprise, for example, linear siloxanes or a lattice-like sol-gel.

In order to assist understanding of the manner in which the sensing layer 34 works, it is instructive to first consider the way in which the sensing layer is made. A polymer layer is spin coated whilst in a fluid state (i.e. before it sets) onto the metal layer 38. During spin coating, surface tension in the fluid polymer mixture helps to ensure that the surface 40 of the sensing layer 34 is substantially flat. This helps to minimise noise or losses in signals returned from the waveguide 12 during use (noise or losses may be caused by scattering due to surface imperfections in the sensing layer). Alternative methods to that of spin coating may be used to apply a polymer layer to the metal layer 38. Such alternative methods include dip coating, spray coating and screen printing.

FIGS. 4*a* to 4*c* show schematically a molecular imprinting process which occurs in the sensing layer 34 during its formation. In a first stage, shown in FIG. 4*a*, entities of a similar or identical structure to the entities to be sensed are mixed with a monomer mixture and a solvent, such that the mixture is in a fluid state. The monomer mixture comprises at least one type of functional monomer and may also comprise at least one type of crosslink monomer. The purpose of a functional monomer within the monomer mixture is different to that of a crosslink monomer, as is discussed in more detail below. The entities which are mixed with the monomer mixture are referred to here as template entities 42. It has been found that an appropriate ratio by mass of components of the monomer mixture is 1:4:20 template entities : functional monomer : crosslink monomer; and that an appropriate ratio by mass of monomer mixture to solvent is 3:4. However, it will be appreciated by those skilled in the art that any other appropriate ratios of constituents of the monomer mixture and solvent may be used.

As mentioned above, the monomer mixture contains functional monomers 44, each of which includes a functional group 46. The monomer mixture may contain more than one type of functional monomer. Each type of functional monomer has a different functional group 46 (these are represented schematically in FIG. 4*a* by different shapes). The functional groups 46 are complementary to functional groups 48 of the template entities 42. Although three types of template entity functional group 48 are shown in FIG. 4*a*, the template entity may have any number of types of functional groups.

The monomer functional groups 46, in the presence of the template entity 42, may interact with corresponding template entity functional groups 48 by any one of the following reversible interaction types: (a) reversible covalent bond(s), (b) covalently attached polymerisable binding groups that are activated for non-covalent interaction by template cleavage, (c) electrostatic interactions, (d) hydrophobic or van der Waals interactions (such as hydrogen bonding), (e) co-ordination with a metal centre, (f) co-bonding, which involves covalent and non-covalent bonding, and (g) semi-covalent bonding, when the initial bond formed is covalent and subsequent bonding is non-covalent.

The functional groups 46 of the monomers 44 interact with corresponding functional groups 48 of the template entities 42, causing a plurality of monomers 44 to arrange themselves around each template entity 42 (as is shown in FIG. 4a).

The monomers 44 may have, for example, amino and/or carboxylic acid functional groups. Possible functional monomers can be classified by type, including acrylics, alcohols, saturated alkynes, amines, aryl, carboxylic acids, esters or ethers; or by property including acidic (i.e. methacrylic acid), neutral (i.e. Styrene) or basic (i.e. 4-vinylpyridine). Below is a list of some common functional monomers which may be suitable for use in manufacturing a molecularly imprinted polymer matrix: acrylates (acrylic acid (AA), methacrylic acid (MMA), trifluoromethyl acrylic acid (TFMAA), methylene-2-succinique acid (MSA), N,N'-dimethylamino-ethyl methacrylate (DMA)), acrylamides (acrylamide (AAm), 2-acrylamido-2-methyl-1-propane sulphonique acid (AMPSA), N-(2-aminoethyl)-methacrylamide (2AEMA) diethylaminoethyl methacrylate (DAEMA)), styrenes (4-vinyl benzoic acid (4VBA), 2-(4-vinylphenyl)-1,3-propanediol (4ES), (4-vinylphenyl(-methyl amine MN' diacetique acid (VPMADA), N,N'-diethyl-(4-vinyl phenyl) amidine (D4VPA), 4-(1,4,7-triazacyclononane-methyl) styrene (4TCMS), 4-vinyl phenylborique acid (VPBA)), Pyridines and imidazoles (4-vinyl pyridine (4VP), 2-vinyl pyridine (2VP), 1-vinyl imidazole (1VI), 4-vinyl imidazole (4VI)).

As previously mentioned, the monomer mixture may also contain at least one type of crosslink monomer. The crosslink monomers help to prevent any distortion in the polymer matrix as it is formed and thereby helps to maintain the shape of any structures formed during the imprinting process. Common crosslink polymers which may be used in creating an appropriate molecularly imprinted polymer matrix include: Ethylene glycol diemethacrylate (EDMA), p-divinylbenzene (DVB), N,N'-ethylenebis(prop-2-eneamide) (EPEA), Tetraethoxysilane (TEOS), Trimethylolpropane trimethacrylate (TRIM), N,N'-methylene bisacrylamide (MBA), p,p'-diisocyanatodiphenylmethane) (DIDM), Bisacryloyl piperazine (BAP) and N,N,-methylene diacrylamide (methylenebisacrylamide).

The solvent, which may also be known as a porogen, may dissolve all the constituents of the monomer mixture. One of the solvent's roles is to generate pores within the fabricated polymer. As such, the solvent can affect the structure of the resultant polymer. For example, acetonitrile as a solvent in acryalate networks leads to a more macro-porous structure than chloroform. Suitable solvents may include: toluene, methylene chloride, chloroform, acetonitrile, acetic acid, methanol, ethanol, dimethylformamide, and water. These can be used individually or in combination with one another.

In certain embodiments of the invention, it may be desirable to include additional additives in the monomer mixture. For example, a plasticiser may be included to reduce the glass transition temperature of the resultant polymer and hence decrease the internal viscosity, thereby increasing its bulk flexibility.

In a next stage, shown in FIG. 4b, the monomer mixture 44 is polymerised and cross-linked with the template entities 42 in situ. This forms a solid polymer matrix 50 containing a plurality of cavities 52 which are of a size and configuration that is capable of receiving the template entities 42, and hence the entities to be sensed. An example of a polymerisation process which may be used is free radical polymerization. However, any appropriate polymerisation process may be used, as will be appreciated by a person skilled in the art.

In the case of free radical polymerisation, polymerisation is initiated by the addition of an initiator compound, which under specific conditions gives rise to free radicals. The conditions required may, for example, be a thermal change or photochemical change as a result of irradiation of the initiator. Where the initiator is involved in a photochemical reaction due to irradiation it is known as a photoinitiator. In some cases, the change in conditions results in uni-molecular bond cleavage of the initiator to yield free radicals. In other cases, the initiator is involved in a biomolecular reaction where an excited state of the initiator interacts with a second molecule (a co-initiator) to generate free radicals. An example thermal free radical initiator is alpha, alpha'-Azoisobutyronitrile (AIBN), and an example photo-initiator is 2,2-Dimethoxy-2-phenylacetophenone (DMPA).

The range of free radical initiators is extensive, and any appropriate initiator can be used. The choice of initiator may depend on many factors including the initiator's solubility in a particular solvent or its decomposition process. The decomposition process may be of particular relevance if the decomposition process is sensitive to temperatures which are similar to that at which mixing of monomers 44 with the template entities 42 is performed. For example, if the decomposition process of an initiator has an activation energy which is too low, then premature free radical production, and hence polymerisation, may occur before the monomers have interacted with the template entities. Premature polymerisation is undesirable since it may mean that the cavities 52 are not properly formed, and hence the polymer is not imprinted with the template entities 42. This may result in the cavities 52 being unable to receive the entities to be sensed.

The initiator may be chosen such that it has a weak bond which, when broken, produces free radicals (the term 'weak bond' should be interpreted as meaning a bond which is weaker than bonds (or other interactions) between the template entities 42 and monomers 44). Where this is done, energy used to initiate the polymerisation by producing the free radicals will not break any of the bonds (or other interactions) between the monomers 44 and the template entities 42.

As will be appreciated by those skilled in the art, there are many free radical types which may be used. Once the free radicals are produced by the initiator, the polymerisation process proceeds in a conventional manner. The free radicals turn some of the monomers into radicals (by removing electrons from them), which can then bond with other monomers to create larger chain radicals. These in turn may then further react with other monomers or chain radicals, and so on in a cascade-type manner. The cascade-type reaction may be terminated in a number of ways, the most common of which is the reaction of two radicals with one another. The chemistry of free radical polymerisation is well known within the art and consequently further detail is not included here.

The above description relates to the use of organic monomers in creating the molecularly imprinted polymer. As previously mentioned, it is also possible to create the polymer using inorganic monomers, for example silicon alkoxide monomers. Such suitable monomers include: Tetraethyoxysilane (TEOS), 3 -aminopropyltriethoxysilane (APTES), 3-methacryloxypropyltrimethoxysilane and 3-(Trimethoxysilyl)propyl methacrylate (MEMO/TMSM), Methyltrimethoxysilanes (MTMOS), phenyl trimethoxysilane (PTMOS), Tetramethoxysilane (TMOS), methyltriethoxy-silane (MTEOS), (3-glycidoxypropyl) trimethoxysilane (GPTMS), Vinyltriethoxysilane (VTEOS), Phenyltrimethoxysilane (TMPS), Ethyltrimethoxysilanes (ETMOS) and Butyltrimethoxysilanes (BTMOS). The polymers produced by these monomers are referred to as sol-gels. It has been found that by controlling the pH and volume of solvent (generally water) used in the monomer mixture, it is possible to affect the porosity of the resultant sol-gel. For example the use of a monomer mixture containing a high volume of water which is at a high pH will produce a more porous material. Examples of monomer mixtures which may be used (and the ratio between quantities of each monomer) include: TEOS:$H_2$O: Ethanol (1:4:4), and TEOS:APTES:PTMOS, (30:1:1.5).

To create a sol-gel, the monomer mixture is made to undergo a hydrolysis reaction and a condensation reaction. A catalyst may be used as part of the hydrolysis reaction. The type of catalyst used may influence the structure of the resultant sol-gel. For example, using HF instead of HCL as the catalyst promotes faster gelation times and/or larger pores in the resultant sol-gel.

Any appropriate solvent may be used in the monomer mixture. Suitable solvents include: water, n-heptane, tetrahydrofuran (THF), methanol (MeOH), Ammonium Hydroxide ($NH_4OH$), Ethoxyethanol, Ethanol, Dodecylbenzene, Acetonitrile, Acetone and Dichloromethane.

Once the sol-gel has been created, it must be dried. The drying process may have an effect on the structure of the final sol-gel, since drying may cause shrinkage. If the shrinkage is substantial, it may affect the sol-gel's ability to receive target entities. Various additives may be added to the monomer mixture to control the rate of drying, and thereby reduce the likelihood that substantial shrinkage takes place during drying. Theses additives, which are generally known as Drying Control Chemical Additives (DCCAs), may for example be formamide, dimethylform amide (DMF), acetonitrile or oxalic acid. Surfactants may also be used. Drying may be carried out in a controlled pressure environment.

A final stage which is common to both organic and non-organic polymers is shown in FIG. 4c. In this final stage, the template entities 42 are removed (e.g. by rinsing) from the polymer matrix 50. This may be done in various ways. For example, a solvent may be used in order to swell the polymer 50 and therefore increase the size of the cavities 52, thereby allowing the template entities 42 to be rinsed out. Upon drying (removal of the solvent from the polymer 50), the cavities 52 may return to their original size (i.e. their size before the polymer was caused to swell by the solvent). Alternatively, the template entities 42 may be broken down and rinsed out. A suitable reagent to break down protein type target entities 42 may be protease. A strong acid which does not damage the structure of the polymer could be used to break down the target entities 42. One reagent of this type which has been found to work is a 1:9 mixture of acetic acid and methanol in which the polymer matrix 50 is allowed to soak for two hours.

Other methods which may be use to remove the template entities 42 from the polymer matrix 50 include: washing the polymer 50 with a fluid which competes more highly for at least one of the functional groups of the template entities 42 than the polymer; exposing the polymer 50 to an agent which causes the bond between the template entities 42 and the polymer matrix 50 to cleave; and exposing the polymer 50 to an agent which causes the bond between the template entities 42 and the polymer matrix 50 to be destroyed.

Silicon based polymers tend to be harder, less porous, less elastic and less flexible than similar carbon based polymers and for this reason it may be more difficult to rinse out the template entities 42 from silicon based polymers than from carbon based polymers. However, the length of the chains used to form the silicon-based polymers may be selected such that sufficient flexibility is present in the polymer to allow template entities 42 to be rinsed from it.

After the template entities have been removed from the polymer matrix 50, the polymer matrix may be dried (for example at room temperature under vacuum).

After the template entities 42 have been removed, the polymer 50 is left with a plurality of cavities 52 containing an arrangement of functional groups 46 which is complementary to the shape and arrangement of functional groups of the entity to be sensed. Each cavity 52 and its corresponding functional groups 46 is referred to hereafter as a reception site 54.

The molecular imprinting process, particularly monomer mixing and polymerisation, may be performed at a temperature which is sufficiently low that little or no thermal energy is available to reverse interactions once they have occurred between the functional monomers 44 and the template entities 42. Reversal of these interactions is undesirable since it will result in the formation of reception sites 54 which are less capable of selectively receiving target entities 56. For this reason, the polymerisation may for example be initiated using UV light instead of using an increase of temperature.

The following are specific examples of techniques for fabricating a molecularly imprinted polymer sensing layer:

In each of the following examples, the metal layer 38 is cleaned prior to forming the polymer sensing layer. Cleaning is a multi-stage process in which the substrate 36 and metal layer 38 is sequentially washed in baths containing different solutions, each for a period of 30 minutes. The solution sequence used is: 2% by volume neutral cleaner (such as SODOSIL®) in aqueous solution, deionised water, isopropanol, deionised water, ethanol, deionised water in an ultrasonic bath, sodium hydroxide, deionised water, 1M hydrochloric acid and finally deionised water. The substrate 36 is then dried in a nitrogen atmosphere.

EXAMPLE 1

A stamp substrate (not shown) is cleaned according to the method described above. The stamp substrate is then incubated in a solution containing the template entities 42. In this example the template entities are RNase A. The RNase solution is a phosphate buffered saline solution which contains 0.05 mg/ml of RNase A. The stamp substrate is exposed to the RNase solution for two hours at room temperature. The coated stamp substrate is then dried in a nitrogen atmosphere. In some embodiments, the RNase coated stamp substrate may subsequently be further coated with a protective sugar layer. A suitable sugar for this purpose is disaccharide, a 1M solution of which, for example, can be spin-coated over the RNase. The protective sugar layer helps to maintain the shape of the RNase, thus improving the structure of any resulting molecularly imprinted polymer.

A monomer mixture is created in which cross-linking monomers EGDMA, TEGDMA PEG400DMA and/or PEG600DMA are mixed with functional monomers 4VP, MMA and/or SM. Photo initiator DMPA is then added to the mixture such that it is about 0.5% of the monomer mixture by weight. Four micro litres of the monomer solution is pipetted onto a suitably cleaned surface, e.g. that of a glass slide cleaned according to the method described above. The coated stamp substrate is then brought into contact with the monomer mixture, first at a small angle (less than 15°) to prevent entrapping bubbles, and then flattened. In this way, the monomer mixture merges with the target entities which are coated onto the stamp substrate. The glass slide, monomer mixture and stamp substrate are then placed in a spin coating machine and rotated at speeds of up to approximately 8500 rpm to produce a very flat surface of the monomer mixture. The spin coating of the monomer mixture onto the glass slide is performed in a nitrogen atmosphere. The stamp substrate and monomer mixture coated on the glass slide are then exposed under an ultraviolet light source (UVA filtered) at an intensity of 75 mW/cm$^2$ for a period of 10 minutes, in order cause the monomer mixture to polymerise so as to produce the molecularly imprinted polymer layer. After polymerisation, the glass slide is removed. The molecularly imprinted polymer layer is then attached to the metal layer 38 on the substrate 36 using a suitable refractive index matched adhesive. The stamp substrate is then removed, exposing the imprinted surface. Alternatively, in some embodiments the molecularly imprinted polymer layer may be coated with a metal film, the substrate 36 then being attached to this metal film using a suitable index matched adhesive. Where this is done, the metal film constitutes the metal layer 38. As a further alternative, the monomer mixture may be pipetted directly onto the metal layer 38 on the substrate 36. In this case, the stamp substrate is brought into contact with the monomer mixture on the metal layer 38 and the monomer mixture is spin coated onto the metal layer of the substrate and subsequently polymerised as before. Once polymerisation is complete, the stamp substrate can be removed, leaving the molecularly imprinted polymer layer in situ on the metal layer 38 on the substrate 36.

In order to remove the RNase template entities, an aqueous eluting solution of 0.8% sodium hydroxide and 2% sodium dodecyl sulphate is used. The polymer is washed with 50 ml of the eluting solution at 80° C. for 30 min. Once this is completed, the polymer is stabilised by being washed three times in deionised water for 5 min. This completes fabrication of the molecularly imprinted polymer layer. If the sensing layer is not to be used straight away, it may be stored in a phosphate buffered saline solution.

EXAMPLE 2

In an alternative example, the RNase A molecularly imprinted polymer layer is formed as an inorganic polymer. A polysiloxane layer (which may be referred to as a scaffold) is fabricated in a two-step process and coated on to the metal layer 38 on a substrate 36. First, a pre-hydrolysis solution is mixed which comprises 1.32 ml of TEOS (cross link monomer), 0.235 ml of deionised water (solvent), 0.33 ml of 0.1M HCl (catalyst) and 0.4 ml of absolute ethanol (co-solvent). The pre-hydrolysis solution is allowed to stand at room temperature for 24 hours. Subsequently, the pre-hydrolysis mixture is mixed with a solution containing 0.33 ml of c-aminopropyltriethoxysilane (APS) (functional monomer) and 1 ml of 0.1M and sodium docecylsulfate (SDS) (foaming agent used to generate macroporosity). The resultant mixture is vortex mixed so as to both mix the silane components and to foam the sol. After the mixture has been merged with the target entities and coated on to the glass slide or metal layer (e.g. as described above in Example 1), gelation occurs. The polymer is then aged at room temperature for 24 hours and then dried at 40° C. for 48 hours. All samples are then thoroughly washed with phosphate buffered saline (PBS), pH 7.4, to remove debris. If the sensing layer is not for immediate use, it may be stored in the dark (this has been found to increase operational longevity of the sensing layer).

EXAMPLE 3

In a further alternative example, the molecularly imprinted polymer layer is an organic polymer which is molecularly imprinted with caffeine. A monomer mixture is created which contains 0.03 g of caffeine (template entity), 0.54 g of methacrylic acid (MMA) (functional monomer), 5.64 g of ethylene glycol dimethacrylate (EDMA) (crosslink monomer), 0.1 g of DMPA (photo initiator) and 1 ml to 20 ml of chloroform (porogenic solvent). The monomer mixture is then allowed to stand for at least 48 hours. Following this the mixture is degassed in a sonicating bath for 30 minutes and then flushed with nitrogen for 5 minutes.

Since the monomer mixture is mixed directly with the template mixture, there is no need to use a stamp substrate (although this method would also work). Instead, two hundred micro litres of the monomer mixture is then spin coated onto to metal layer 38 on the substrate 36 at 3600 rpm for a period of 1 minute. Whilst the monomer mixture is being spin coated, UV illumination at 360 nm is used to initiate the polymerisation process.

Once the polymer layer has been formed, the template entities are removed using a mixture of methanol and acetic acid in the ratio 4:1 by volume, with which the polymer is washed for up to 24 hours. The time that it takes for the template entities to be washed out of the polymer layer is dependant on the thickness of the polymer layer. The thinner the layer, the less time it will take to wash out the template entities. For example, the polymer layer produced in this example requires washing for a period of 10 minutes. Another method of removing the template entities is by using sequential washing with individual solvents such as acetic acid, acetonitrile, phosphoric acid, methanol, ethanol, and tetrahydrofuran. The surface of the polymer may have a final wash with a buffer solution or distilled water as required.

In this example, functional binding within the molecularly imprinted polymer with caffeine predominately results from the hydrogen atom of the carboxyl group of MMA forming a hydrogen bond with the oxygen atom of the carbonyl group of caffeine. However, other electrostatic forces and hydrophobic π-π interactions may also contribute.

EXAMPLE 4

In a further example the molecularly imprinted polymer layer is an inorganic caffeine-imprinted polymer. This is fabricated by creating a monomer mixture comprising: 7.2 g water (solvent) with added hydrochloric acid to establish a pH of 1.2, 20.8 g TEOS (monomer) and 14.4 g ethanol (co-solvent). The monomer mixture is mixed with caffeine and stirred for 24 hours to allow the reaction to take place. Since the monomer mixture is mixed directly with the template mixture, there is no need to use a stamp substrate (although this method would also work). Instead, a portion of the monomer mixture including caffeine template entities is spin coated onto the metal layer 38 on a substrate 36. The polymer is then dried in a sealed oven for 24 hours at 60° C. After drying, the polymer is allowed to stand at room temperature for at least 12 hours so that it stabilises.

It has been found that the performance of the resultant polymer is enhanced if the monomer mixture is acidic (pH 1-6). The acceptance of caffeine into the resultant polymer has been found to decrease with increasing solvent polarity. This is thought to be because polar additives can interfere with the hydrogen bond interactions between the template entities and the functional monomers within the monomer mixture.

Once the polymer has been formed, the template entities are eluted by washing the polymer in ethanol. Alternatively, the template entities may be removed by calcination at 600°

C. The porosity of the imprinted polymer may be improved by washing it with lactic acid (it is thought that this may loosen the silica network).

EXAMPLE 5

In a further example, the molecularly imprinted polymer layer is a paraoxon imprinted sol-gel. The monomer mixture is created as follows: 3 ml of TEOS (monomer), equivalent to 13.5 mmol, is mixed with 200 µl of PTMOS (monomer), equivalent to 1.2 mmol, and 3 ml of ethanol (co-solvent) until clear. 100 µl of concentrated hydrochloric acid is then added in order to make the mixture acidic. 200 µl of APTES (monomer), equivalent to 0.9 mmol, is then added along with 1 ml of water (co-solvent). The mixture is degassed in a sonicating bath for up to 30 min, and then flushed with nitrogen for 5 minutes. Then, 2 ml of the monomer mixture is mixed with 200 µL ethanolic solution of paraoxon, equivalent to 0.02 mmol. The mixture is allowed to stand for 24 hours. Next, 30 µl of the reacted monomer mixture is spin coated on to a metal layer 38 on a substrate 36 at 4000 rpm for 20 seconds. This was found to create a polymer film of thickness 534+/−6 nm. The coated substrate is then allowed to dry at room temperature for 24 hours. The paraoxon is extracted from the imprinted sol-gel using a Soxhlet extractor with ethanol.

EXAMPLE 6

A similar paraoxon imprinted sol-gel can be created using a monomer mixture as follows: Three millilitres of TMOS (monomer), equivalent to 20.3 mmol, is mixed with 3 ml of 2-ethoxy ethanol (co-solvent), 370 µl of PTMOS (monomer), equivalent to 2.2 mmol, and 420 µl of TMOS-CTAC (monomer), equivalent to 0.6 mmol, until clear. One millilitre of 0.1M hydrochloric acid and 1 ml of water (co-solvent) are then added. The mixture is then stirred for 2 hours at room temperature and degassed in a sonicating bath for up to 30 min, and then flushed with nitrogen for 5 minutes. Subsequently, 2 ml of the monomer mixture is mixed with 200 µl of 0.1M ethanolic solution of paraoxon. Subsequently, 30 µl of the reacted monomer mixture is spin coated on a cleaned metal layer 38 on a substrate 36 at 4000 rpm for 20 seconds. It has been found that this creates a polymer film with a thickness of 534+/−6 nm. The coated substrate is then dried at room temperature for 24 hours. Again, the paraoxon is extracted from the imprinted sol-gel by Soxhlet extraction with ethanol.

It has been found that the TEOS based sol-gel hydrolyses more slowly under acidic hydrolysis conditions than TMOS based sol-gel.

EXAMPLE 7

A further alternative method for producing a paraoxon imprinted sol-gel is to use a monomer mixture consisting of the following substances; TMOS:PhTMOS:APTES:ethanol: hydrochloric acid:water in a molar ratio of 1:0.1:0.1:4:0.003: 4. Once an ethanolic solution of paraoxon has been added, the reacted monomer mixture can be spin coated on to a metal layer 38 on a substrate 36 at 4000 rpm for 20-60 seconds. Once the sol-gel has dried, the template paraoxon molecules can be extracted in ethanol. Alternatively, they may be extracted by washing in a 50% by volume aqueous solution of methanol containing 1.0 M of potassium hydroxide for up to 24 hours.

EXAMPLE 8

In a further example, the molecularly imprinted polymer layer is a cholesterol imprinted organic polymer. The method is substantially the same as that explained above for other organic polymers. The monomer mixture comprises: 0.387 g of cholesterol (template), 0.682 ml of methacrylic acid MMA (functional monomer), 4.72 ml of EGDMA (cross link monomer), 0.05 g AIBN (thermal initiator) or DMPA (UV initiator); and 7.5 ml of chloroform (solvent). Alternative solvents may be used, such as ethanol, toluene, heptane, or hexane. The cholesterol solvent mixing may be performed for example at up to 60° C. (this may help to ensure that the cholesterol is completely dissolved). Alternative functional monomers that may be used include 4-vinylpyridine, styrene, and Cyclodextrin. Alternative crosslink monomers that may be used include Ethylvinylbenzene, divinylbenzene, trimethylolpropane, and trimethacrylate. After the polymerisation, the chloroform is removed and the polymer is dried in a vacuum oven for 12 hours at room temperature.

EXAMPLE 9

A cholesterol imprinted sol-gel may be fabricated with the following monomer mixture: 41.7 g of TEOS (equivalent to 200 mmol) and 40.8 g of acetic anhydride (equivalent to 400 mmol) mixed at 140° C. for 12 hours, followed by 7.73 g of cholesterol (equivalent to 20 mmol). These components are mixed for a time period of up to 2 days and then allowed to set dry at up to 60° C.

EXAMPLE 10

Alternatively, a cholesterol imprinted sol-gel may be fabricated with the following monomer mixture: 10.4 g TEOS (equivalent to 50 mmol), 50 ml of THF, 9 ml of distilled water and 0.01 ml of aqueous ammonia solution (25% by weight) as catalyst, followed by 1.93 g of Cholesterol, equivalent to 5 mmol.

The template entity may be removed from an inorganic cholesterol imprinted polymer by washing the polymer with a mixture of acetic acid and tetrahydrofuran at 1:1 volumetric ratio, or chloroform and acetic acid at 4:1 volumetric ratio. Alternative substances which may be used for template removal include acetonitrile, tetrahydrofuran, methanol, acetic acid, acetone and ethanol.

Referring again to FIG. 2, silanes may be used to aide adhesion of the imprinted polymer layer 34 to the metal layer 38. For example 3-(Trimethoxysilyl)propyl methacrylate (MPS) may be used to aid in metal to polymer (or glass to polymer) adhesion. Other silanes, such as Vinyltrimethoxysilane (VTS), aid with corrosion resistance properties of the resultant polymer. A method of applying silanes comprises adding a small portion to a suitable solvent, for example to a mixture of 95% ethanol and 5% water mixture by volume. This mixture can then be added to the monomer mixture. Another method involves an extra production step, wherein the silane layer is separately provided on top of the metal layer 38. The molecularly imprinted polymer is then coated on top of the silane layer.

Once the molecularly imprinted polymer has been formed, it may be used as a sensing layer. FIG. 5 shows the manner in which a cavity 52 of the molecularly imprinted polymer 50 receives and retains a target entity. The cavity 52 and corresponding functional groups 46 in combination are referred to herein as a reception site 54. A target entity 56 (i.e. an entity to be sensed) fits within the reception site 54, and in addition has functional groups 57 which are complementary to those of the reception site 54 in terms of both their type and relative positioning. Other entities which do not have the required combination of shape and reception sites will not be received and retained in the cavity (the entities will either pass through the cavity or will not enter the cavity).

It is not necessarily the case that each reception site 54 is identical. In the process by which the reception sites 54 are formed (see FIG. 4*a*), the monomers 44 arrange themselves around the template entity 42 randomly, governed only by interactions between functional groups of the monomers 44 and corresponding functional groups on the template entities 42. As such, the exact size and shape of the cavity 52, as well as the position, orientation and type of corresponding functional groups 46 which form a particular reception site 54 may vary.

In order for the reception sites 54 to function so as to receive a target entity in a retainable manner, it is desirable that the cavity 52 is large enough to receive the target entity 56 and that the relative position and type of functional groups 46 of the reception site 54 correspond with functional groups 57 of the target entities 56. For this reason it may be possible to use a template entity 42 which is different to the target entity 56 when forming the molecularly imprinted polymer (and hence the reception sites 54). However, where this is done, the reception sites thereby created should have a size capable of receiving the target entity 56 and have functional groups 46 of a relative positioning and type that they may interact with corresponding functional groups 57 on the target entity.

In one particular embodiment, the target entity 56 is ribonuclease (also known as RNase). However, the target entity may be any chosen bio-molecule. For example, the target entity may be any enzyme, including alkaline phosphatase (ALP). Both RNase and ALP are relatively large bio-molecules with molecular weights of more than 500 g per mol. However, the target entity 56 may be a smaller molecule (e.g. having a molecular weight of less than 500 g per mol). Examples of smaller molecules include organophosphates (for example paraoxon) and alkaloids (for example caffeine).

Depending on the porosity of the molecularly imprinted polymer layer, a relatively small target entity 56 may be sufficiently small that it is able to diffuse into the reception sites 54 within in the matrix 50, whereas a relatively large target entity may be too large to enable it to diffuse into the matrix 50. Where the target entity 56 is too large to enable it to diffuse into the matrix 50 the target entities 56 may still be received by molecularly imprinted reception sites on the surface of the matrix 50. The molecularly imprinted polymer may thereby allow the presence of the target entity to be sensed.

The molecularly imprinted polymer may form part of an optical sensor, for example as described further above in relation to FIG. 1. The optical sensor may for example form part of a purification system that is used to produce very pure water (for example to be used in chemical assay applications). The optical sensor may for example be configured to monitor for the presence in the water of contaminants such as biological agents (including bacteria), or the endo-toxins which they produce. In order to detect a wide variety of bacteria, even if they are no longer living, it is possible to detect entities which are constituents of bacteria. One such example is RNase. RNase is an enzyme used by bacteria to catalyse the hydrolysis of ribonucleic acid, or RNA, into smaller components. The bacteria both secrete RNase whilst living and release RNase when they decompose. As such the presence of RNase is an indicator as to the presence of live bacteria or bacteria which has died. The optical sensor may be configured to detect the presence of RNase in the water.

Referring again to FIG. 2, a waveguide 12 of an optical sensor comprises a molecularly imprinted polymer layer 34 provided on a metal layer 38. The waveguide 12 is situated in flow communication with a conduit 32 through which a fluid 31 flows (flow denoted by arrow A). The metal layer 38 is provided on a substrate 36. RNase 56 is present in water 31 within a conduit 32 (the conduit may form part of a water purification system). As the water 31 and suspended RNase 56 flow through the conduit, the water and RNase may flow into the molecularly imprinted polymer layer 34 (via a porous surface 40 of the layer). The molecularly imprinted polymer layer 34 includes a plurality of reception sites 54. As the RNase 56 moves through the molecularly imprinted polymer layer 34, the RNase passes through reception sites 54. The orientation of the RNase may be changing, and the RNase may pass through a number of reception sites 54 having different orientations. The RNase 56 may encounter a reception site having an orientation and functional groups 46 arranged such that it interacts with the functional groups and is retained within the reception site 54.

FIG. 3 corresponds to FIG. 2, but shows several reception sites 54 which have received and retained RNase 56. Although not shown in FIG. 3, RNase 56 may also be received and retained by reception sites 54 which are at the surface of the molecularly imprinted polymer layer 34. If the molecularly imprinted polymer layer is not porous enough to permit the RNase to pass into the layer via the surface 40 then the RNase may only be received and retained by the reception sites 54 which at the surface 40 of the layer 34.

The retention of target entities 56 by the molecularly imprinted polymer layer 34 alters optical properties of the molecularly imprinted polymer layer. This affects the way in which the propagating light travels through the waveguide 12, thereby allowing modification of a parameter of the light to be measured. For example the refractive index of the molecularly imprinted polymer layer 34 may change, which in turn may modify the intensity of light seen by a detector 30 (see FIG. 1). In one example, RNase 56 is retained by a reception site 54. This causes water which was previously present within the reception site 54 to be displaced. Since the refractive index of the RNase 56 is different from the refractive index of water, the refractive index of the molecularly imprinted polymer layer 34 is changed. This allows the presence of the RNase 56 in the molecularly imprinted polymer layer 34 to be detected optically.

In order to optically detect the presence of a target entity (e.g. RNase) in the sensing layer 34, light is directed into the waveguide 12 using the apparatus shown in FIG. 1. The light is directed at the waveguide 12 at a particular incident angle B (see FIG. 2) such that it couples through the metal layer 38 and into the molecularly imprinted polymer layer 34 to excite a guided mode within the waveguide 12 (i.e. is coupled into the guided mode). The incident angle B which provides coupling into the guided mode may be referred to as the resonant incident angle.

The guided mode is centred within the molecularly imprinted polymer layer 34. The guided mode is a leaky mode, and consequently some light couples out of the guided mode. The light is coupled out of the guided mode with an exit angle C which is equal which is equal to the resonant incident angle B. The value of the resonant incident angle B at which light couples into the guided mode (and hence the value of the exit angle C) will change if the refractive index of the molecularly imprinted polymer layer 34 changes.

Light incident on the waveguide 12 which is not coupled to the leaky guided mode may be reflected from the waveguide 12.

When light is coupled into the guided mode at the resonant incident angle B, and then subsequently coupled out again, it undergoes a phase shift. The metal layer 38 acts to convert this phase shift into a change of intensity. This allows the presence of resonant coupling into the waveguide to be detected using an intensity detector.

The metal layer 38 has a refractive index which is considerably higher than that of the polymer layer 34. This higher refractive index of the metal layer 38, compared with the polymer layer 34, causes light travelling within the polymer layer 34 to be reflected from the boundary between the polymer layer and the metal layer. Thus, light travelling within the polymer layer 34 will travel further within the polymer layer before it is coupled out of the polymer layer.

Increasing the size of the refractive index difference between the metal layer 38 and the polymer layer 34 will increase the reflectivity of the boundary between the polymer layer and the metal layer. Increasing the reflectivity of the boundary between the polymer layer and the metal will cause light to travel further within the polymer layer before it is coupled out of the polymer layer 34. This in turn increases the interaction between the light and the polymer layer 34, thereby increasing the sensitivity of the waveguide to changes in an optical property of the polymer layer.

The majority of the refractive index of the metal layer 38 arises from the complex component of the refractive index. Consequently, the metal layer 38 is absorptive of the light which is directed at the waveguide 12 (considerably more absorptive than the polymer layer 34). The metal layer is provided with a sufficiently small thickness that a significant portion of the light directed at the waveguide 12 can pass through the metal layer 38 and couple into the polymer layer 34 (and also pass back through the metal layer).

Although the waveguide shown in FIGS. 2 and 3 has a metal layer, any appropriate material layer may be used instead of the metal layer 38. The material used should have a higher refractive index than the polymer layer 34. The material layer should be sufficiently thin that it allows a significant portion of the light directed at the waveguide 12 to pass into the polymer layer 34. Examples of suitable materials include dyes and carbon nanotubes (in addition to metals).

Metals tend to have a high refractive index over a large range of wavelengths, whereas dyes tend to have a high refractive index for a relatively narrow range of wavelengths. Consequently, a waveguide having a metal layer may be used in conjunction with light over a wider range of wavelengths than a waveguide having a dye layer.

In an alternative arrangement, the metal layer 38 is not present in the waveguide. Where this is the case, the phase shift may for example be detected by using a second polariser 28 which is located between the waveguide and the detector 30. The second polariser 28 may be crossed with respect to the first polariser 22 (located between the light source 16 and the waveguide 12), such that it only transmits light which has undergone a phase change. This allows the presence of resonant coupling into the waveguide to be detected using an intensity detector. The phase shift may alternatively be detected using other means, for example an interferometer such as a Michelson interferometer or a Mach-Zender interferometer.

If a leaky guided mode is excited in the waveguide 12 using incident light at a resonant incident angle B, this will be seen as a peak (or in some circumstances a dip) in the intensity of light detected at that angle C. If a metal layer 38 is present in the waveguide 12, the refractive index of the metal layer (amongst other things) may determine whether a peak is seen or a dip is seen.

FIGS. 6 to 8 are graphs which show different schemes of reflectivity of the waveguide 12 depending on the refractive index of the metal layer 38. The graphs, which were generated using simulations, show the reflectivity (R) of the waveguide 12 as a function of the incident angle B (denoted here by $\theta$). Other variables are kept constant, including the thickness of both the metal and sensing layers, and the refractive index of the sensing layer. FIG. 6 shows the relationship between the reflectivity and incidence angle for a metal layer 38 with a real component of refractive index which is less than about 0.7 (e.g. gold). FIG. 7 shows the relationship between the reflectivity and incidence angle for a metal layer 38 with a real component of refractive index which is between about 0.7 and about 1.4 (e.g. aluminium). FIG. 8 shows the relationship between the reflectivity and incidence angle for a metal layer 38 with a real component of refractive index which is greater than about 1.5 (e.g. titanium).

The peaks and troughs of the graphs shown in FIGS. 6 to 8 are indicative of the resonant incident angle B of the waveguide 12, since there is a fixed relationship between the peaks or troughs and the resonant incident angle B. As can be seen from the graphs, in some instances it may be easier to detect a peak of reflected intensity, and in other instances it may be easier to detect a dip of reflected intensity. In this description, detection of a peak of reflected intensity is described. However, detection of a dip of reflected intensity may equivalently be performed.

The resonant incident angle B at which light couples into a leaky guided mode is dependent upon optical properties of the sensing layer 34, and in particular the refractive index of the sensing layer. Referring to FIG. 3, the target entities 56 (e.g. RNase) have a higher refractive index than water 31. Therefore, when the RNase displaces the water in the reception sites 54, the refractive index of the sensing layer 34 increases. This increase of refractive index changes the resonant incident angle B at which a leaky guided mode may be excited in the waveguide 12 (and correspondingly changes the angle C at which light is coupled from the guided mode). This means that the presence of RNase (or other target entity) in the water 31 (or other fluid) may be indicated by a change of the resonant incident angle B required to excite a leaky guide mode in the waveguide.

The change of the resonant incident angle B may be seen by directing light at the waveguide 12 over a range of angles, and measuring the light which is output from the waveguide over a range of angles. Alternatively, it may be seen by directing light into the waveguide 12 at the resonant incidence angle and monitoring the light output from the waveguide (either light coupled back out from the waveguide or light transmitted from an end of the waveguide). Where this approach is used, the change in refractive index of the sensing layer 34 will reduce the amount of light coupled into the guided mode, since the angle at which the light is directed towards the waveguide will no longer be the resonant angle. This will be seen as a change of intensity of light reflected from the waveguide (or a change of intensity of the light transmitted from an end of the waveguide).

FIG. 9 is a graph which shows movement of the angle at which a peak of reflected intensity is seen from a waveguide which embodies the invention. The movement of the peak of reflected intensity is measured in terms of pixels of a detector. The movement of the peak is measured for samples within which caffeine has been dissolved in ethanol with different concentrations. Unshaded disks in FIG. 9 are results obtained with a waveguide which had a polymer layer that been molecularly imprinted with caffeine (produced in accordance with example 3 above). Shaded disks in FIG. 9 are results obtained with a waveguide which had a polymer layer which had not been molecularly imprinted (referred to hereafter as non-imprinted polymer (NIP)). The waveguide with NIP was produced in accordance with example 3 above, but without the inclusion of caffeine in the monomer mixture before polymerisation.

The results were obtained by directing light into each waveguide using the apparatus shown in FIG. 1. Light was directed at the waveguide over a range of incident angles. The detector 30 used was a CCD array. Changes in the resonant incident angle of the waveguide mode were measured by measuring a shift in the position of the pixel within the CCD array which measured the greatest intensity of incident light (this pixel is hereafter referred to as the peak pixel). The shift of the position of the peak pixel was measured relative to the position of the peak pixel that was seen when no caffeine was present in the ethanol.

The position of the peak pixel was measured using the waveguide with the NIP polymer layer. Before measuring the position of the peak pixel, the NIP polymer layer 34 of the waveguide was exposed for a period of 10 minutes to one of a group of solutions of caffeine dissolved in ethanol of different concentration. The concentrations of caffeine used were $10^{-6}$M, $10^{-5}$M, $10^{-4}$M, $10^{-3}$M and $10^{-2}$M. Since there are no reception sites 54 for the caffeine within the NIP polymer layer, no change in the refractive index of the polymer layer (and hence no change in the resonant incident angle) should be seen. The positions of the peak pixel measured for the waveguide with the NIP polymer layer exposed to each concentration of caffeine solution were compared with the peak pixel position measured when no caffeine was present in the ethanol.

The position of the peak pixel was measured using the waveguide having the caffeine sensitive molecularly imprinted polymer layer 34 in accordance with an embodiment of the present invention. Again, before the position of the peak pixel was measured, the polymer layer 34 was exposed for 10 minutes to one of a group of solutions of caffeine dissolved in ethanol with different concentrations. Again, the concentrations of caffeine used were $10^{-6}$M, $10^{-5}$M, $10^{-4}$M, $10^{-3}$M and $10^{-2}$M. Since the molecularly imprinted polymer layer was made using caffeine as the template entity, caffeine is a target entity for the polymer layer 34. It is believed that 10 minutes is sufficient time for a significant number of caffeine molecules to bind with the reception sites 54 in this case. In other cases other exposure times may be used (for example up to 24 hours). The caffeine molecules which are received by the reception sites 54 alter the refractive index of the polymer layer 34 and hence change the resonant incident angle B at which light is coupled into the waveguide 12. As can be seen from the unshaded disks of FIG. 9, the measured position of the peak pixel increased as the concentration of the caffeine solution increased.

FIG. 10 shows, as a function of the concentration of caffeine solution, the difference between the position of the pixel peak for the waveguide with the caffeine sensitive molecularly imprinted polymer layer and the position of the pixel peak of the waveguide with the NIP polymer layer. The line which joins the points is a best fit line which was generated using a 3 parameter sigmoid fit. The graph of FIG. 10 shows that the waveguide with the molecularly imprinted polymer layer exhibits a measurable movement of the peak pixel if it is exposed to the caffeine target entity at concentrations of about $5 \times 10^{-4}$M and above for a period of 10 minutes. It is believed that a measurable movement of the peak pixel may also be achieved by exposing the polymer layer 34 to a lesser concentration of caffeine but for a period of time which is longer than 10 minutes.

A sensor according to the present invention may be used as part of a purification system. For example, in the case of water, if RNase (or other target entity) is detected in the water, then the water is known to be contaminated. In this case the water is disposed of, and the purification system used to purify the water is cleaned in order to remove the contamination. It should be noted that the sensor may be used as part of a purification system which purifies any chosen liquid.

The change in refractive index of the polymer layer 34 due to the presence of entities to be sensed results from the displacement from the reception sites 54 of the liquid, which has a particular refractive index, by the target entities which have a different refractive index. In the described embodiment the liquid is water, and the target entities have a refractive index which is greater than water. As such, when the water is displaced by the target entities the refractive index of the polymer layer 34 increases. However, if the liquid were to have a greater refractive index than the target entities, the target entities will cause in a reduction in the refractive index of the polymer layer 34 when they are received in reception sites 54. The detection of a reduction in the refractive index of the polymer layer 34 may be detected in an analogous way to that of the detection of an increase in the refractive index of the polymer layer 34.

The use of an optical sensor to detect contaminants within a water purification system provides two benefits. Firstly, it is not limited to detecting a specific type of bacteria, but can instead detect a wide range of bacteria (since it senses products of their existence and/or decomposition). As such, not only can a wide range of bacteria be detected, but they can also be detected if they have recently ceased to be living. Secondly, unlike many tests for RNase which currently exist, the RNase does not have to be active for it to be detected. Current tests rely on using the action of RNase within a reaction in order to show its presence. However, embodiments of the invention do not require the RNase to be active, since it is only the shape and relative orientation of the functional groups which is needed in order for the RNase to be received in the reception sites 54 and hence detected. As such, RNase that is denatured can be detected as readily as active RNase. This has the advantage that the RNase can be detected in a wide range of environments, for example over a range of temperature and pH values. The RNase may also be detected in a variety of solvent types. This eliminates the need for additional reagents such as buffers, and enables the detection of RNase to be performed in water.

The absence of a requirement for reagents and special environmental conditions when detecting RNase provides the additional benefit that the sensor 10 can form part of a continuous detection regime. In a continuous detection regime the sensor 10 is in communication within a conduit 32 through which fluid (e.g. water) continuously flows. The detector provides a continuous output signal which indicates in real time the presence (or otherwise) of a target entity in the fluid.

The strength of interaction(s) between target entities 56 and the molecularly imprinted reception sites 54 may be high. Consequently, it may not be possible in some instances to remove the target entities 56 once they have been retained in reception sites 54. In this situation the optical sensor 10, or at least the waveguide 12 portion of it, will be a single use device and may be replaced once contamination has been detected.

In some instances it may be possible to remove the target entities 56 using a process similar to that used to remove the template entity 42 during the molecular imprinting process. Where this is done, the optical sensor 10 may be reused. The process for removing the target entities may comprise preventing fluid containing target entities from flowing past the sensor 10, and then flowing an alternative fluid past the sensor 10. The alternative fluid contains a reagent suitable for removing bound target entities 56 from the reception sites 54. Once the target entities are removed, the flow of the alternative fluid is stopped. Normal operation of the sensor 10 is then resumed.

FIGS. 11 and 12 schematically show two alternative ways in which the waveguide 12 may be constructed. In FIG. 11 the waveguide 12 comprises a metal layer 38, a molecularly imprinted polymer layer 34 and a conduit 32 through which fluid 31 may flow (in use the conduit contains water or some other fluid). The conduit 32 may take the form of a flow cell (not shown) which may be attached to the molecularly imprinted polymer layer 34 in a fluid-tight manner. A guided mode 59 is centred on the molecularly imprinted polymer layer 34, which has a higher refractive index than the fluid in the conduit 31.

In FIG. 12, the waveguide 12 comprises a metal layer 38, waveguiding layer 58, molecularly imprinted polymer layer 34 and conduit 32. The waveguiding layer 58 is located between the metal layer 38 and the molecularly imprinted polymer layer 34, and has a higher refractive index than the molecularly imprinted polymer layer. A guided mode is centred on the waveguiding layer 58, and an evanescent component of the guided mode extends into the molecularly imprinted polymer layer.

The alternative waveguide constructions shown in FIGS. 11 and 12 function in similar ways. A difference between them is that the sensitivity of the waveguide shown in FIG. 11 is higher than that of the waveguide shown in FIG. 12, since more light passes into the molecularly imprinted polymer layer 34. In other words, in the embodiment shown in FIG. 11, since the molecularly imprinted polymer layer 34 is one and the same as the waveguiding layer 58, the interaction between the molecularly imprinted polymer layer 34 and the incident light is stronger, resulting in a greater sensitivity to the target entities.

As previously discussed, the resonant incident angle of a waveguide which forms part of an optical sensor in accordance with the present invention is dependent on the refractive index of the molecularly imprinted polymer layer. Other factors may also influence the resonant incident angle.

FIGS. 13 and 14 are graphs which show the response of three different waveguides. In particular, FIGS. 13 and 14 show graphs of measured radiation intensity as a function of incident angle for the three waveguides. The results shown in these graphs were obtained by directing light into each waveguide using the apparatus shown in FIG. 1. Light was directed at each waveguide over a range of incident angles. In this case, the light source used was a laser and the intensity of the light was measured in arbitrary units by the detector.

Each of the waveguides had a molecularly imprinted layer which was a caffeine imprinted sol-gel layer made according to the method detailed in Example 4 above. Each waveguide was the same except that each was formed by spin coating the molecularly imprinted polymer layer onto the metal layer at a different speed and/or for a different period of time. Spin coating the molecularly imprinted polymer onto the metal layer under different conditions (e.g. different spin speed and/or for a different period of time) may affect the thickness of the formed molecularly imprinted layer and/or the extent and/or severity of any surface imperfections on the surface of the formed molecularly imprinted polymer layer. Other variables were kept constant, including the thickness of the metal layer.

Within FIG. 13, lines 80, 81 and 82 show the responses of three separate waveguides which have been fabricated by spin coating the molecularly imprinted polymer layer for 30 seconds at 8000 rpm, for 20 seconds at 7000 rpm, and for 30 seconds at 7000 rpm respectively. The responses of the waveguides are shown as a function of external coupling angle. Referring to FIG. 1, the external coupling angle is the angle between the normal to the surface of the waveguide 12 and the direction at which the input light from the light source 16 is incident on the prism 14.

Within FIG. 14, lines 83, 84 and 85 show the responses of the same waveguides as in FIG. 13, wherein the waveguides have been fabricated by spin coating the molecularly imprinted polymer layer for 30 seconds at 8000 rpm, for 20 seconds at 7000 rpm, and for 30 seconds at 7000 rpm respectively. The responses of the waveguides are shown as a function of internal coupling angle. Referring to FIG. 1, the internal coupling angle is the angle between the normal to the surface of the waveguide 12 and the direction at which the input light from the light source 16 passes through the prism 14 as it travels towards the waveguide 12.

FIGS. 13 and 14 show that the resonant incident angle of the waveguides (which is related to the position of each respective peak within the graphs) is affected by the conditions used to spin coat the molecularly imprinted polymer layer. In particular, the graphs show that the waveguide which has a molecularly imprinted polymer layer which is spin coated for a shorter time (20 seconds) has a resonant incident angle which is less by approximately 2 degrees than the resonant incident angles for the waveguides which are spin coated for a longer time (30 seconds).

The graphs of FIGS. 13 and 14 also show that the measured intensity of light which is output from the waveguide which has a molecularly imprinted polymer layer which is spin coated for a shorter time (20 seconds) is less than the measured intensity of light which is output from the waveguide which has a molecularly imprinted polymer layer which is spin coated for a longer time (30 seconds).

The greater resonant incident angle and greater light output intensity of the waveguides which are spin coated for a relatively long time may result from the fact that increasing the spin coating time decreases the extent and/or severity of any surface imperfections on the surface of the formed molecularly imprinted polymer layer. By reducing the extent and/or severity of any surface imperfections, this will result in the surface of the molecularly imprinted polymer layer being flatter. By making the surface of the molecularly imprinted polymer layer flatter, this may reduce the amount of light incident on the surface of the molecularly imprinted polymer layer which is scattered by the surface. Increasing the spin coating time may also reduce the thickness of the of the formed molecularly imprinted polymer layer.

FIGS. 15 and 16 are graphs which show the response of a waveguide in four different conditions. In particular, the graphs show measured radiation intensity as a function of incident angle for the waveguide in the four different conditions. The results were obtained by directing light into each waveguide using the apparatus shown in FIG. 1. Light was directed at each waveguide over a range of incident angles. In this case, the light source used was a laser and the intensity of the light was measured in arbitrary units by the detector.

The waveguide which was used to obtain the results shown in FIGS. 15 and 16 had a molecularly imprinted layer which was a caffeine imprinted sol-gel layer made according to the method detailed in Example 4 above. The first condition in which the response of the waveguide was measured was when the molecularly imprinted polymer layer of the waveguide had been washed with water after the waveguide had been created. The second condition in which the response of the waveguide was measured was when the molecularly imprinted polymer layer had been washed with water and then ethanol. The third condition in which the response of the waveguide was measured was that the molecularly imprinted polymer layer had been washed with water, then ethanol, and had then been exposed to a caffeine solution for a period of 1 minute. The fourth condition in which the response of the waveguide was measured was that the molecularly imprinted polymer layer had been washed with water, then ethanol, and had then been exposed to a caffeine solution for 5 minutes.

Within FIGS. 15 and 16, lines 86 and 90 show the response of the waveguide in the first condition; lines 87 and 91 show the response of the waveguide in the second condition; lines 88 and 92 show the response of the waveguide in the third condition and lines 89 and 93 show the response of the waveguide in the fourth condition.

The responses of the waveguide in different conditions shown in FIG. 15 are shown as a function of external coupling angle. Referring to FIG. 1, the external coupling angle is the angle between the normal to the surface of the waveguide 12 and the direction at which the input light from the light source 16 is incident on the prism 14. The responses of the waveguide in different conditions shown in FIG. 16 are shown as a function of internal coupling angle. Referring to FIG. 1, the internal coupling angle is the angle between the normal to the surface of the waveguide 12 and the direction at which the input light from the light source 16 passes through the prism 14.

FIGS. 15 and 16 show that the resonant incident angle of the waveguide (which is related to the position of each respective peak within the graphs) is greater for the two conditions (third and fourth conditions) of the waveguide where the molecularly imprinted polymer layers have been exposed to the caffeine, compared to that of the conditions of the waveguide in which the molecularly imprinted layer has only been washed with water, or with washed with water and ethanol respectively. In particular, the conditions (third and fourth conditions) of the waveguide which have molecularly imprinted polymer layers which have been exposed to the caffeine have resonant incident angles which are approximately 0.5 degrees greater than those in which the molecularly imprinted polymer layer has only been washed with water (first condition), or with water and ethanol (second condition) respectively. As previously discussed, this is because the caffeine binds with the reception sites in the molecularly imprinted polymer layer and thereby increases the refractive index of the molecularly imprinted polymer layer.

Furthermore, it can be seen that the resonant incident angle of the waveguide is greater for the fourth condition of the waveguide (which is related to the position of the peak of each of lines 89 and 93) than it is for the third condition of the waveguide (which is related to the position of each of the peaks of lines 88 and 92). It is thought that this is because the waveguide in the fourth condition was exposed to the target entity (caffeine) solution for longer than the waveguide in the third condition. Because of this, there was a greater opportunity for the target entities (caffeine) to bind with the reception sites of the waveguide in the fourth condition compared to the waveguide in the third condition. For this reason, more target entities (caffeine) may bind with the waveguide in the fourth condition than with the waveguide in the third condition, thus increasing the refractive index of the waveguide in the fourth condition to a greater extent than that of the waveguide in the third condition.

In the above description, resonant coupling of light into a leaky guided mode has been used to provide detection of a change of the refractive index of the sensing layer. In an alternative arrangement surface plasmon resonance may be used to detect the change of refractive index. Surface plasmons are surface electromagnetic waves that propagate along an interface between a metal and a dielectric. Since the electromagnetic waves are on the boundary of the metal and the dielectric, they are very sensitive to any change at this boundary. A waveguide may be constructed in which the molecularly imprinted polymer layer is located on the metal layer, and surface plasmon resonance is used to detect changes of an optical property of the molecularly imprinted polymer layer.

Other optical detection mechanisms may be used to detect the change of refractive index (or other optical property) of the molecularly imprinted polymer layer.

A waveguide which provides a leaky guided mode allows the use of materials with a relatively low refractive index to form the molecularly imprinted polymer layer 34 or waveguiding layer 58 compared with those used for surface plasmon resonance. This may make it easier to use a wide variety of materials, including for example polymer, sol-gel, or hydro-gel.

A further advantage of using a leaky guided mode is that, because there is a relatively small difference between the refractive index of the sensing layer 34 and of the fluid 31, the resonance angle at which the leaky mode is excited is relatively sharp. The term 'relatively sharp' is intended to mean sharper than that which would be achieved if surface plasmon resonance were used as the detection mechanism.

Surface plasmon resonance sensors may be difficult to use, since they utilize a very thin metal layer, the thickness of which cannot easily be selected. The metal layer thickness in combination with the angle of at which incident light falls on the surface plasmon resonance sensor determines the penetration depth of an evanescent wave component of the surface mode which interacts with the molecularly imprinted polymer layer. Varying the angle of the incident light typically allows the penetration depth of the evanescent wave to be tuned from several microns to several tens of nanometers. Since the metal layer thickness cannot be easily varied, the range of penetration depths of the evanescent wave and hence the detection depth cannot be easily selected.

In contrast to this, when a leaky waveguide is used it is predominantly the thickness of the waveguiding layer which controls the penetration of the evanescent light. Since the molecularly imprinted polymer layer 34 is relatively thick compared to that of the metal layer in surface plasmon resonance, its thickness, and hence the evanescent wave penetration depth above the waveguiding layer, can be more easily controlled. In general the thickness of the waveguiding layer of a leaky waveguide is around ten times thicker than the metal layer used in a surface plasmon resonance construction. The element of control of the penetration of the evanescent wave is useful when a construction such as that shown in FIG. 12 is used, since it allows the degree of penetration of the light into the molecularly imprinted polymer layer to be controlled. The use of a thick waveguiding layer is particularly advantageous when measuring a change in refractive index of the molecularly imprinted polymer layer (the waveguiding layer and molecularly imprinted polymer layer being one and the same in this case). This is due to the fact that, in general, the greater the thickness of the waveguiding layer, the higher the order of mode which can be carried by the waveguiding layer. The higher the order of mode which can be carried within the waveguiding layer, the greater the proportion of light incident on the waveguide that remains within the waveguiding layer and hence the greater the sensitivity of the sensor to a change in refractive index of the waveguiding layer.

In the case of Surface Plasmon Resonance, the light directed at the sensor is Transverse Magnetic (TM) polarised light.

A disadvantage of known leaky mode waveguides is that in some instances detection optics are required to detect a dip in the intensity of light returned from the waveguide, and to follow angular movement of that dip. The absence of light is inherently more difficult to detect than a peak of light intensity. Use of the metal layer 38 to provide a peak in light intensity when a leaky waveguide mode is excited may thus be advantageous.

Dimensions of the waveguide may selected such that they excite a variety of numbers of modes. Dimensions of the waveguide may be selected so as to determine the penetration depth of an evanescent wave. Selection of appropriate dimensions for the waveguide may depend upon the wavelength of light used. A light source 16 which is substantially monochromatic may be used. Examples of monochromatic light sources include LASERs and RCLEDs (resonant cavity light emitting diodes).

Although specific examples of waveguide structures have been given in the above description, other suitable waveguide structures may be used.

Although the above description refers to the detection of RNase, in water, other target entities may be detected. The target entities may be in a fluid other than water.

Although the molecularly imprinted polymer layer is described as being porous, it may be possible to use a non-porous molecularly imprinted polymer layer. Where this is done, the target entities will be received only at the upper surface of the molecularly imprinted polymer layer, and the resulting signal will therefore be less strong than that which is provided by the illustrated embodiments of the invention. Whether the molecularly imprinted polymer layer may be considered to be porous is dependant on whether the target entities can diffuse through the molecularly imprinted polymer layer. One factor which is relevant in determining whether this is the case is the relative size of the cavities 52 and the target entities. In general, the molecularly imprinted polymer layer is more likely to be porous if the cavities 52 are of the same order in size or larger than the target entities. If the molecularly imprinted polymer layer is not porous then any trapping of target entities by the molecularly imprinted polymer layer will happen at the surface of the molecularly imprinted polymer layer. In such situations, it may be desirable to have a waveguiding (molecularly imprinted polymer layer) layer which is of a thickness which is capable of carrying only a single mode. This will maximise the evanescent component of the light incident on the waveguide and hence increase the sensitivity of the sensor to target entities which are at the edge of or outside the waveguiding layer.

Although described embodiments of the invention relate to a waveguide having a molecularly imprinted polymer layer, the invention may alternatively comprise a non-polymer layer which has been molecularly imprinted.

The invention claimed is:

1. An optical sensor comprising a leaky mode waveguide having a sensing layer which is molecularly imprinted such that it will receive and retain target entities to be sensed, the optical sensor further comprising a detection apparatus arranged to detect a change of an optical property of the leaky mode waveguide which occurs when the target entities are received and retained in the sensing layer, and wherein the optical sensor forms part of a contamination detector which is part of a purification system.

2. An optical sensor as claimed in claim 1, wherein the sensing layer comprises reception sites having shapes which are suitable for receiving the target entities.

3. An optical sensor as claimed in claim 1, wherein the sensing layer comprises reception sites having functional groups which are complementary to functional groups of the target entities.

4. An optical sensor as claimed in claim 1, wherein the sensing layer is porous.

5. An optical sensor as claimed in claim 1, wherein the target entities are ribonuclease.

6. An optical sensor as claimed in claim 1, wherein the target entities are inactive.

7. An optical sensor as claimed in claim 1, wherein the leaky mode waveguide includes a layer of material having a refractive index which is higher than the refractive index of the sensing layer.

8. An optical sensor as claimed in claim 7, wherein the layer of material is a metal layer.

9. An optical sensor as claimed in claim 1, wherein the sensing layer is a polymer layer.

* * * * *